US010265213B2

United States Patent
Shim et al.

(10) Patent No.: US 10,265,213 B2
(45) Date of Patent: Apr. 23, 2019

(54) TEMPOROMANDIBULAR JOINT CORRECTION APPARATUS WITH EXCHANGEABLE ADJUSTOR

(71) Applicants: Yoon Seob Shim, Incheon (KR); So Hee Shim, Incheon (KR)

(72) Inventors: Yoon Seob Shim, Incheon (KR); So Hee Shim, Incheon (KR)

(73) Assignee: Jae Il Lim, Incheon (KR)

( * ) Notice: Subject to any disclaimer, the term of this patent is extended or adjusted under 35 U.S.C. 154(b) by 469 days.

(21) Appl. No.: 15/081,510

(22) Filed: Mar. 25, 2016

(65) Prior Publication Data
US 2017/0273819 A1    Sep. 28, 2017

(51) Int. Cl.
*A61C 7/08* (2006.01)
*A61C 7/36* (2006.01)
*A61F 5/56* (2006.01)

(52) U.S. Cl.
CPC ............... *A61F 5/566* (2013.01); *A61C 7/08* (2013.01); *A61C 7/36* (2013.01)

(58) Field of Classification Search
CPC ...... A61F 5/566; A61F 2005/563; A61F 5/56; A61C 7/08; A61C 7/36; A63B 71/085; A63B 71/081
See application file for complete search history.

(56) References Cited

U.S. PATENT DOCUMENTS

| 6,099,304 | A  | * | 8/2000 | Carter | A61C 7/36 433/19 |
| 6,394,799 | B1 | * | 5/2002 | Testa | A61C 7/00 433/19 |
| 2002/0000230 | A1 | * | 1/2002 | Gaskell | A61F 5/566 128/848 |
| 2007/0235037 | A1 | * | 10/2007 | Thornton | A61F 5/566 128/848 |
| 2010/0300458 | A1 | * | 12/2010 | Stubbs | A61F 5/566 128/848 |
| 2011/0168187 | A1 | * | 7/2011 | Nelissen | A61F 5/566 128/848 |
| 2011/0220125 | A1 | * | 9/2011 | Van Dyke | A61F 5/566 128/848 |

(Continued)

FOREIGN PATENT DOCUMENTS

| KR | 10-0596129 | 7/2006 |
| KR | 20-2010-0006504 | 6/2010 |

(Continued)

OTHER PUBLICATIONS

English translation of 10-0596129.

(Continued)

*Primary Examiner* — Tarla R Patel
(74) *Attorney, Agent, or Firm* — Antonio Ha & U.S. Patent, LLC

(57) ABSTRACT

According to an embodiment of the present disclosure, a temporomandibular joint (TMJ) correction apparatus comprises an upper guard including an upper coupler provided at an end of the upper guard, the upper coupler including a protrusion projecting laterally, a lower guard including a lower coupler provided at an end of the lower guard, and an adjustor detachably coupled with the tower coupler and supported by the protrusion.

11 Claims, 13 Drawing Sheets

(56) References Cited

U.S. PATENT DOCUMENTS

| | | | | |
|---|---|---|---|---|
| 2012/0227750 A1* | 9/2012 | Tucker | ............... | A61F 5/566 128/848 |
| 2013/0112210 A1* | 5/2013 | Stein | ............... | A61F 5/566 128/848 |
| 2014/0230829 A1* | 8/2014 | Rogers | ............... | A61F 5/566 128/848 |
| 2015/0075540 A1* | 3/2015 | Dye | ............... | A61F 5/566 128/848 |
| 2015/0216716 A1* | 8/2015 | Anitua Aldecoa | ...... | A61F 5/566 128/848 |
| 2017/0000643 A1* | 1/2017 | Gelb | ............... | A61F 5/566 |
| 2017/0367793 A1* | 12/2017 | Veis | ............... | A61F 5/566 |
| 2018/0168845 A1* | 6/2018 | Hofmann | ............... | A61F 5/566 |

FOREIGN PATENT DOCUMENTS

| | | |
|---|---|---|
| KR | 10-2011-0031427 | 3/2011 |
| KR | 10-2012-0033386 | 4/2012 |

OTHER PUBLICATIONS

English translation of 10-2012-0033386.
English translation of 10-2011-0031427.
English translation of 20-2010-0006504.

\* cited by examiner $D_1 < D_2 < D_3 < D_4 < D_5 < D_6 < D_7$

Fig. 9
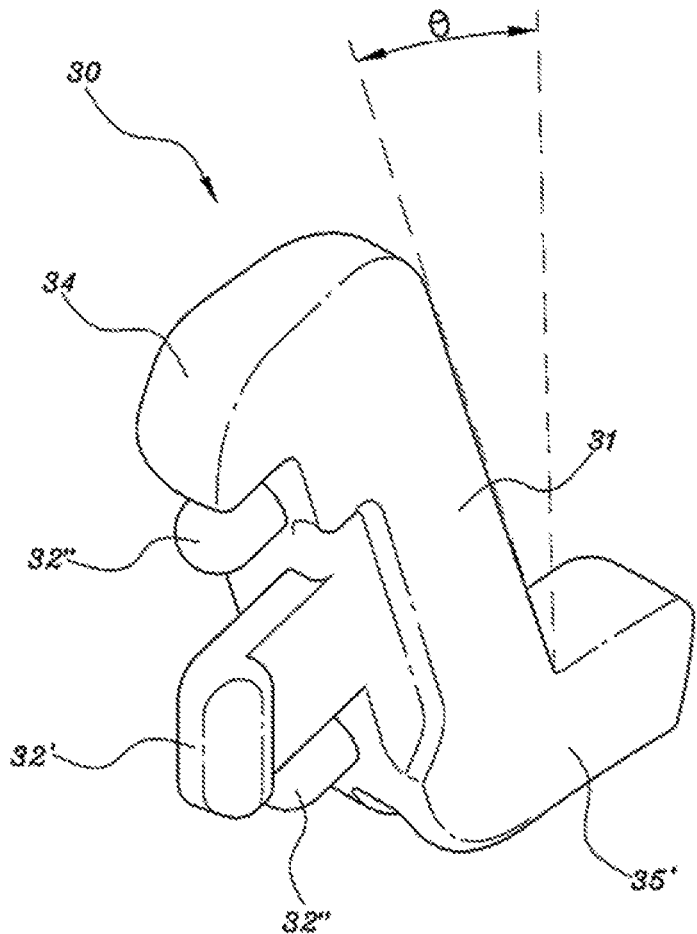
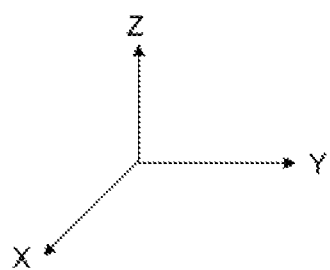

$D_1 < D_2 < D_3 < D_4 < D_5 < D_6 < D_7 < D_8$

TEMPOROMANDIBULAR JOINT CORRECTION APPARATUS WITH EXCHANGEABLE ADJUSTOR

CROSS-REFERENCE TO RELATED APPLICATIONS

This patent application claims priority under 35 U.S.C. § 119 to Korean Patent Application No. 10-2015-0123808, filed on Sep. 1, 2015, in the Korean Intellectual Property Office, the disclosure of which is incorporated by reference herein in its entirety.

TECHNICAL FIELD

Embodiments of the present disclosure concern treating temporomandibular joint (TMJ) disorder, and more specifically, to TMJ correction apparatuses with an exchangeable adjustor.

DISCUSSION OF RELATED ART

A lot of folks suffer from one sleep disorder or another but the most common something called sleep apnea. Sleep apnea occurs when the airways become blocked.

There are other reasons that can help to stop sleeping well and these are related to the temporomandibular joint (TMJ). The jaw joints that connect the lower jaw to the skull are the TMJ joints.

A jaw joint disorder could be causing your sleep problems.

If there is a problem with the TMJ, then the pain could cause a TMJ related sleep disorder.

TMJ problems are often caused by a misaligned bite, which can put the tongue in the wrong place so that it readily blocks the airways. Such jaw joint disorder may cause snoring which, when put aside long time, could lead to more serious health issues, including heart disease and high blood pressure.

Therefore, a need exists for an approach for treating such TMJ and resultant snoring issues.

SUMMARY

According to an embodiment of the present disclosure, a temporomandibular joint (TMJ) correction apparatus comprises an upper guard including an upper coupler provided at an end of the upper guard, the upper coupler including a protrusion projecting laterally, a lower guard including a lower coupler provided at an end of the lower guard, and an adjustor detachably coupled with the lower coupler and supported by the protrusion.

The lower coupler may include a side fixture fixed to a side surface of the lower guard and a lower wing positioned ahead of the side surface and coupled with the adjustor.

The lower wing may include a coupling hole formed through a central portion of the lower wing and a coupling trench formed in a rear surface of the lower wing.

The adjustor may include a body, a coupling mechanism protruding frontward from a center portion of the body, a guide extending upward and downward from the body, a bent portion extending frontward from an upper portion of the guide, and a supporting portion extending frontward and rearward from a lower portion of the guide.

The adjustor may include a body, first coupling mechanism and second coupling mechanism protruding frontward from a center portion of the body, a guide extending upward and downward from the body, a bent portion extending frontward from an upper portion of the guide, and a supporting portion extending rearward from a lower portion of the guide. The second coupling mechanism may include an end portion bent laterally.

The adjustor may be exchangeable. The adjustor may have a predetermined thickness suited for a condition or process of correcting a jaw of a user wearing the TMJ correction apparatus.

The predetermined thickness of the adjustor may differ depending on the condition or process of correcting the jaw.

A front surface of the protrusion may be inclined at an acute angle with respect to a Z direction.

The side fixture may include a plurality of protrusions and depressions, and a fixing hole may be formed in the side surface of the lower guard. The plurality of protrusions and depressions may be fitted into the fixing hole.

A rear surface of the lower wing may be inclined at an acute angle with respect to a Z direction.

The coupling mechanism of the adjustor may include a rib and a coupling bump extending from the rib.

The TMJ correction apparatus may further comprise a spacing adjustor between the adjustor and the protrusion.

The spacing adjustor may include a coupling bump on a rear surface thereof, and the protrusion may include a coupling slot on a front surface thereof. The coupling bump of the spacing adjustor may be fitted into the coupling slot of the protrusion.

The adjustor may be coupled or fastened to the protrusion to prevent the upper guard and the lower guard from opening.

The adjustor may include a fixing bump on a rear surface of the body, and the protrusion may include a coupling slot on a front surface thereof. The fixing bump may be fitted into the coupling slot of the protrusion.

The adjustor may include a fixing bump on a rear surface of the body. The protrusion may include a coupling slot on a front surface thereof. The spacing adjustor may include a fixing bump fitting hole on a front surface thereof. The fixing bump may be fitted into the fixing bump tilting hole, and the coupling bump may be fitted into the coupling slot of the protrusion.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings, wherein:

FIG. 9 is a perspective view illustrating an adjustor of a TMJ correction apparatus according to an embodiment of the present disclosure;

DETAILED DESCRIPTION OF EXEMPLARY EMBODIMENTS

Hereinafter, exemplary embodiments of the inventive concept will be described in detail with reference to the accompanying drawings. The inventive concept, however, may be modified in various different ways, and should not be construed as limited to the embodiments set forth herein. As used herein, the singular forms "a," "an," and "the" are intended to include the plural forms as well, unless the context clearly indicates otherwise. It will be understood that when an element or layer is referred to as being "on," "connected to," "coupled to," or "adjacent to" another element or layer, it can be directly on, connected, coupled, or adjacent to the other element or layer, or intervening elements or layers may be present. The same reference denotations may be used to refer to the same or similar elements throughout the specification and the drawings.

Figure 1:
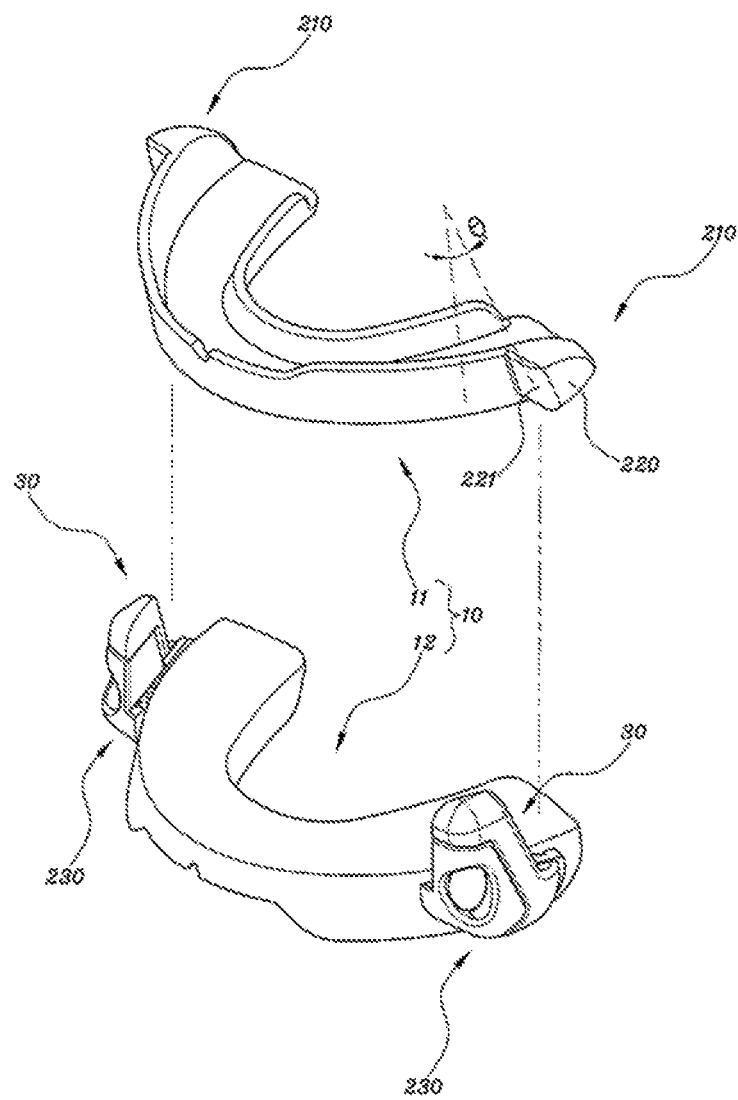
FIG. 1 is an exploded perspective view illustrating a temporomandibular joint (TMJ) correction apparatus according to an embodiment of the present disclosure.
Figure 2:
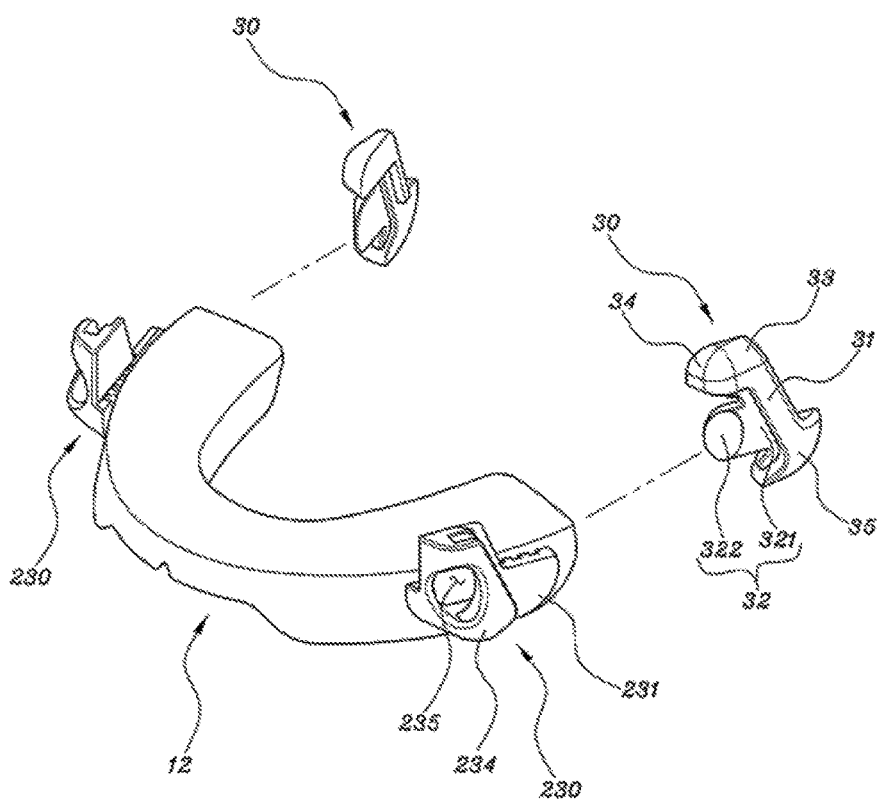
FIG. 2 is an exploded perspective view illustrating, a lower guard of a TMJ correction apparatus according to an embodiment of the present disclosure.
Figure 3:
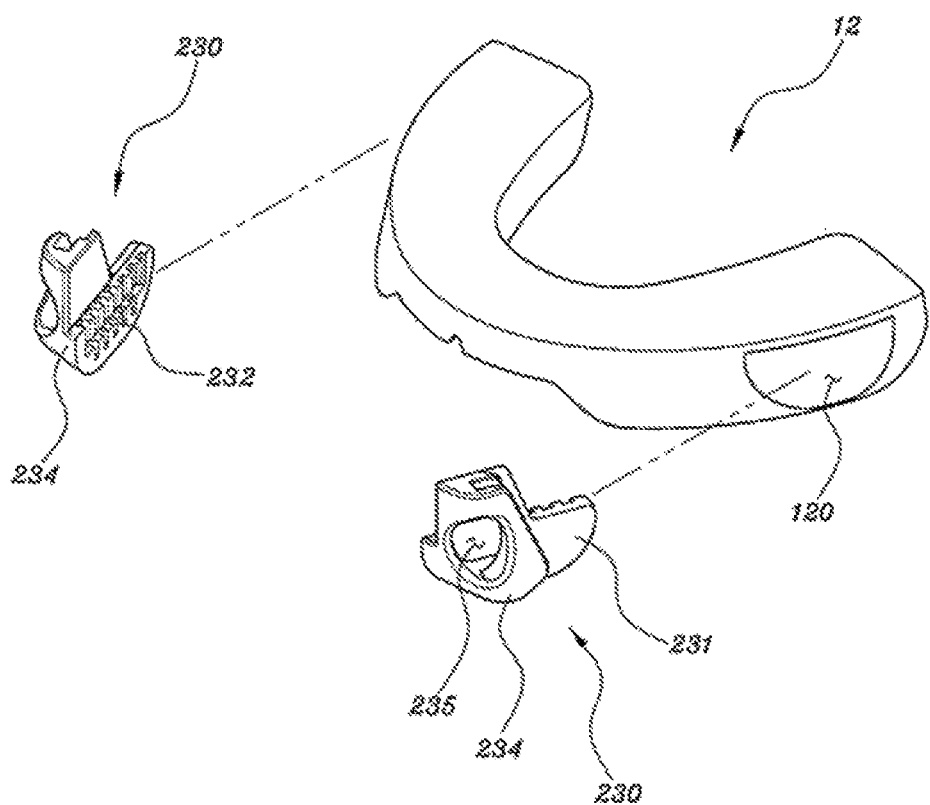
FIG. 3 is an exploded perspective view illustrating a lower guard of a TMJ correction apparatus, wherein lower couplers are dissembled from the lower guard, according to an embodiment of the present disclosure.
Figure 4:
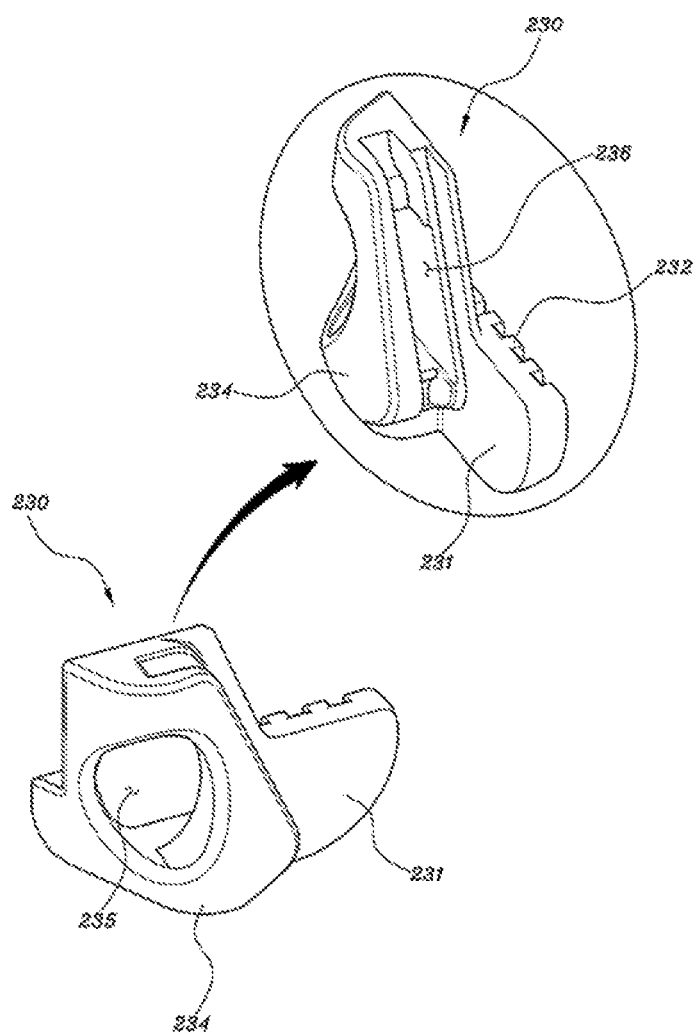
FIG. 4 is an expanded view illustrating a lower coupler of a TMJ correction apparatus according to an embodiment of the present disclosure.
Figure 5:
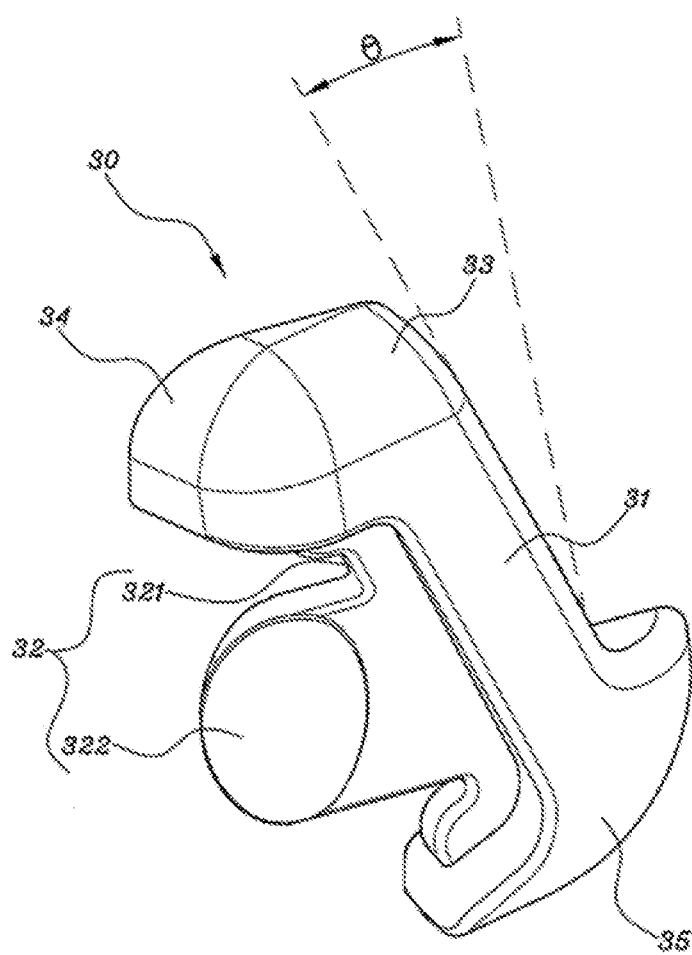
FIG. 5 is an expanded view illustrating an adjustor of a TMJ correction apparatus according to an embodiment of the present disclosure.
Figure 6:
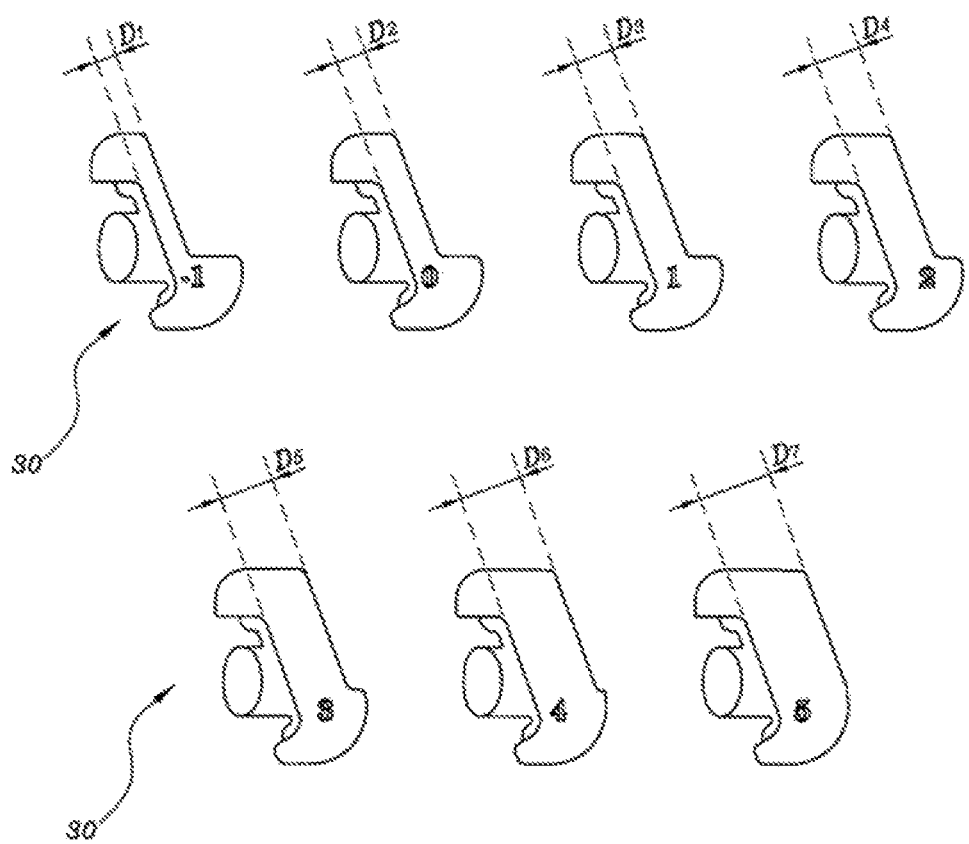
FIG. 6 is a view illustrating adjustors with different thicknesses in a TMJ correction apparatus according to an embodiment of the present disclosure.
Figure 7:
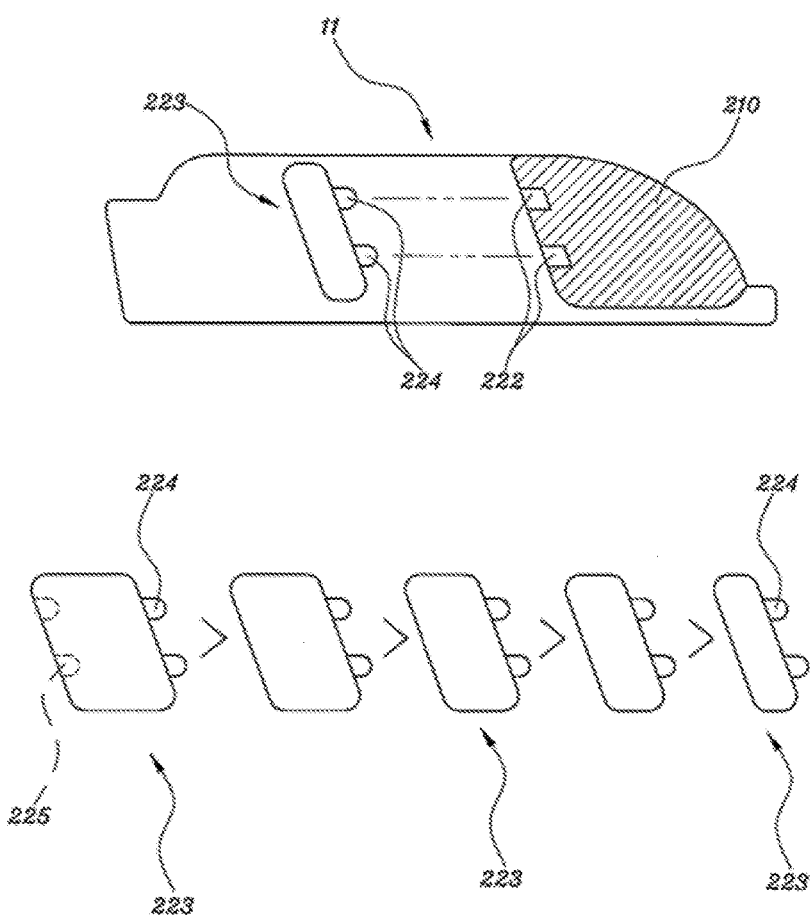
FIG. 7 is a view illustrating spacing adjustors with different thicknesses in a TMJ correction apparatus according to an embodiment of the present disclosure.
Figure 8:
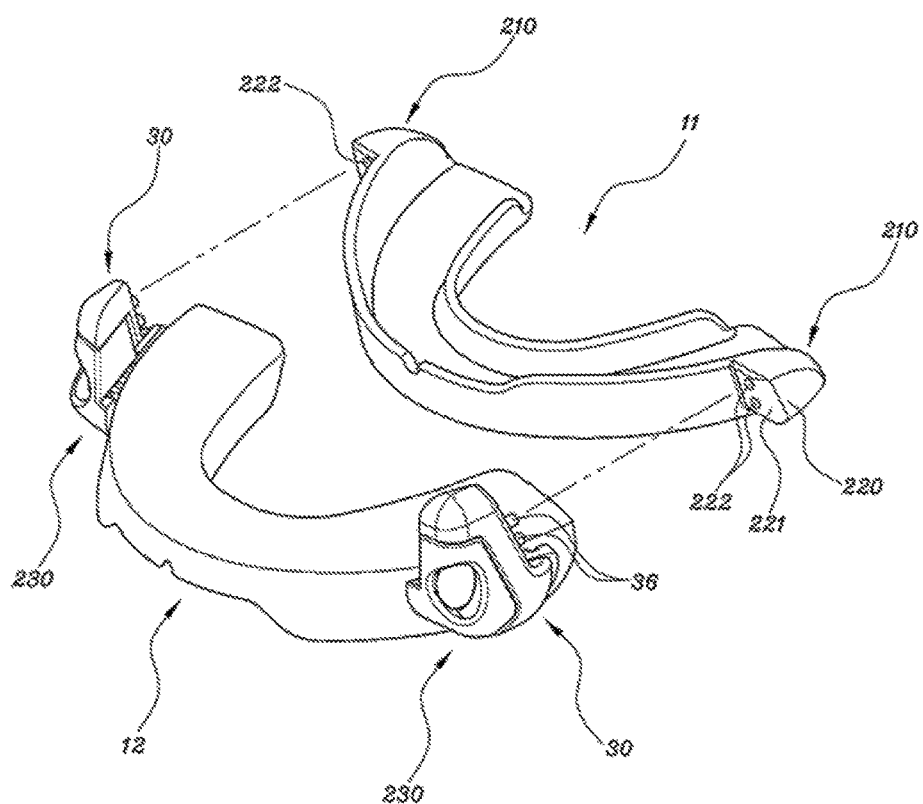
FIG. 8 is a perspective view illustrating a TMJ correction apparatus, wherein an upper guard and a lower guard are separated from each other, according to an embodiment of the present disclosure.

FIG. 1 is an exploded perspective view illustrating a temporomandibular joint (TMJ) correction apparatus according to an embodiment of the present disclosure. FIG. 2 is an exploded perspective view illustrating a lower guard of a TMJ correction apparatus according to an embodiment of the present disclosure. FIG. 3 is an exploded perspective view illustrating a lower guard of a TMJ correction apparatus, wherein lower couplers are dissembled from the lower guard, according, to an embodiment of the present disclosure. FIG. 4 is an expanded view illustrating a lower coupler of a TMJ correction apparatus according to an embodiment of the present disclosure. FIG. 5 is an expanded view illustrating an adjustor of a TMJ correction apparatus according to an embodiment of the present disclosure. FIG. 6 is a view illustrating adjustors with different thicknesses in a TMJ correction apparatus according to an embodiment of the present disclosure. FIG. 7 is a view illustrating spacing adjustors with different thicknesses in a TMJ correction apparatus according. In an embodiment of the present disclosure. FIG. 8 is a perspective view illustrating a TMJ correction apparatus, wherein an upper guard and a lower guard are separated from each other, according to an embodiment of the present disclosure.

The TMJ correction apparatus may be simply referred herein as to a correction apparatus.

Referring to FIG. 1, the correction device 1 includes teeth guards 10, couplers 210 and 230 provided at the respective ends of the teeth guards 10, and adjustors 30 for correcting the TMJ.

The teeth guards 10 include an upper guard 11 for covering the upper teeth and a lower guard 12 covering the lower teeth.

The teeth guards 10 may be formed by molding. For example, molds respectively corresponding to the upper teeth and lower teeth of a patient (also referred herein as to a user) may be manufactured, and a predetermined material, e.g., resin or plastic, may be poured into the molds and is then dried to form the solid teeth guards 10. However, methods for forming the teeth guard 10 are not limited thereto, and other various methods may be used. For example, the upper guard 11 and the lower guard 12 may be formed to have grooves which respectively allow the upper teeth and lower teeth to be placed therein.

The couplers 210 and 230 include upper couplers 210 and lower couplers 230. The upper couplers 210, respectively, are formed at two opposite ends of the upper guard 11 that guard upper molars, and the lower couplers 210, respectively, are formed at two opposite ends of the lower guard 12 that guard lower molars.

The upper couplers 210 may project from the two opposite ends, respectively, of the upper guard 11, and the upper couplers 210 may be integrally formed with the upper guard 11.

However, embodiments of the present disclosure are not limited thereto. Although the upper couplers 211 are integrally formed with the upper guard for the purpose of description, the upper couplers 210 may be configured to be detachably coupled with the upper guard 11 as necessary or considering the condition of the patient's teeth.

The upper couplers 210 may project laterally (e.g., substantially in Y and −Y directions as denoted in the drawings) from the two opposite ends of the upper guard 11 and may support the adjustors 30 from a rear side thereof.

The upper couplers 210, respectively, include protrusions 220 respectively projecting laterally (e.g., substantially Y and −Y directions as denoted in the drawings) from the two opposite ends of the upper guard 11 so that the respective front surfaces of the protrusions 220 support the respective rear surfaces of the adjustors 30.

The front surface of each protrusion 220 may be a tapered surface 221. The from surface of the protrusion 220 may be inclined at an acute angle θ with respect to a vertical line from a top of the front surface to a bottom thereof. For example, the front surface of the protrusion 220 may be inclined at an acute angle θ with respect to the Z direction.

The tapered surface 221 may play a role as a surface to support the rear surface of the adjustor 30 coupled to a side of an end portion of the lower coupler 230.

The lower guard 12 includes the lower couplers 230 respectively projecting laterally from two opposite ends thereof. Each lower coupler 230 includes a side fixture 231 fixed to a side of an end portion of the lower guard 12 and a lower wing 234 fixed to a front portion of a side of the side fixture 231 and coupling with the adjustor 30.

The side fixture 231 and the lower wing 234 may be integrally formed together.

Multiple protrusions and depressions 232 are formed in an inner surface of the side fixture 231. The protrusions and depressions 232 are fitted or fastened into a fixing hole 120 formed in a side of an end portion of the lower guard 12.

The lower wing 234 is a component that abuts the front side of the adjustor 30 to fix the adjustor 30. The adjustor 30 is positioned between the tapered surface 221 of the upper coupler 210 and the lower wing 234 to position the TMJ at a front side.

The lower wing 234 has a coupling hole 235 at a center portion thereof. The coupling hole 235 passes through the lower wing 234 at the center portion of the lower wing 234. A coupling trench 236 is formed in a rear surface of the lower wing 234.

The front side of the adjustor 30 may be detachably coupled to the lower wing 234 through the coupling hole 234 and the coupling trench 236. For example, the rear surface of the lower wing 234 may be tapered at an acute angle θ which is the same as the angle formed by the tapered surface 221 of the front side of the protrusion 220 of the upper coupler 210.

Coupling slots 222 may be formed in the front surface of the protrusion 220 constituting the upper coupler 210 of the upper guard 11. A spacing adjustor 223 may be detachably coupled to the protrusion 220. The spacing adjustor 223 may be positioned between its corresponding wing 234 and its corresponding protrusion 220. Coupling bumps 224 may be formed on a rear surface of the spacing adjustor 223 to be detachably coupled to the coupling slots 222.

Multiple spacing adjustors 223 with different thicknesses or widths may be provided, so that a spacing adjustor 223 with a thickness or width suited for the user or the condition of the user's teeth correction may be put to use.

The TMJ may be adjusted by the adjustors 30, and the TMJ may be further adjusted and the lower guard 12 may be finely positioned by the spacing adjustors 223.

The adjustor 30 may be fitted into its corresponding lower coupler 230 and is backed up from its rear side by the protrusion 220 of the upper coupler 210 to adjust the position of the user's jaw. The adjustor 30 includes a body 31, a coupling mechanism 32 protruding frontward from a center portion of the body 31, a guide 33 extending frontward from an upper portion of the body 31 to form a bent portion 34, and a supporting portion 35 extending frontward and rearward from a lower portion of the body 31.

The adjustor 30 may prevent the respiratory obstruction while the user is in sleep or is correcting his jaws and may keep the user's TMJ sticking out in a front direction to allow the airway a predetermined width.

The TMJ correction apparatus may be worn on the user with a severe snoring issue while be is in sleep or when the user's TMJ needs to be corrected.

The adjustors 30 may be exchanged depending on the condition or process of correction.

For example, one of multiple adjustors 30 respectively having different widths ($D_1$ to $D_N$) may be selectively used depending on the condition or process of correcting the user's TMJ as shown in FIG. 6.

For example, as shown in FIG. 6, multiple adjustors 30 having substantially the same configuration except that they have different widths ($D_1$ to $D_7$) of bodies 31 may, be used.

The widths D1 to D7 may meet the following relation: $D_1 < D_2 < D_3 < D_4 < D_5 < D_6 < D_7$.

The coupling mechanism 32 of the adjustor 30, which protrudes frontward, includes a rib 321 protruding frontward from the body 31 and integrally formed with the body 31 and a coupling bump 322 protruding frontward from a center portion of the rib 321 and shaped substantially as a circle.

The coupling bump 322 may be press-fittingly coupled to the lower wing 234 of the lower coupler 230 through the coupling hole 235.

The lower coupler 230 in which the coupling bump 322 is fitted into the lower wing 234, specifically, the rear surface of the lower coupler 230, may be supported on the tapered surface 221 which is the front surface of the protrusion 220 of the upper coupler 210, so that the lower guard 12 may provide a force for correcting the user's TMJ that acts in a front direction.

For example, upon fixing the user's snoring or correcting the user's TMJ, the degree of sticking out the user's lower jaw may be determined within such a range as not to overburden the TMJ depending on the condition of the user's TMJ.

The upper guard 11, the lower guard 12, and the adjustors 30 suited for the determined degree of sticking out the lower jaw may be selectively used. For example, among multiple adjustors 30 with different widths or thicknesses, an adjustor 30 with a width or thickness suitable for the determined degree of sticking out the lower jaw may be selected, and the selected adjustor 30 may be coupled and fastened to the lower coupler 230 fixed through the fixing hole 120 of the lower guard 12 to be supported by the tapered surface 221 of the protrusion 220 of the lower coupler 210 in the upper guard 11 so that the rear side of the adjustor 30 is not pushed rearwards. In this position, the user wears the teeth guards 10 on his upper and lower teeth.

The user may put on the teeth guards 10 in sleep and take off while he does daily routines, or the user may keep wearing the teeth guards 10 for correcting his TMJ.

Depending on the process or condition of the corrected TMJ, the adjustor 30 with a thickness or width may be replaced with other adjustor 30 with a different thickness or width.

As such, the user may periodically exchange the adjustors 30 with different thicknesses or widths as the TMJ correction proceeds and may secure and accumulate data it treatment based on the periods of exchanging the adjustors 30. Based on the accumulated data, the user may be subject to reliable and precise treatment.

As shown in FIG. 8, the upper guard 11 and the lower guard 12 may need to remain closed depending on the user's condition.

According to an embodiment of the present disclosure, coupling slots 222 may be formed in the front surface of the protrusion 220 constituting the upper coupler 210 of the upper guard 11, and fixing bumps 36 may be formed on a rear surface of the body 31 of the adjustor 30 to be fitted into the coupling slots 222, as shown in FIG. 8. The fixing bumps 36 may be fitted into the coupling slots 222 to couple and fasten the adjustor 30 to the protrusion 220, so that the upper guard 11 and the lower guard. 12 remain in a closed position, thereby preventing the user from mouth breathing.

According to an embodiment of the present disclosure, the spacing adjustor 223 may be detachably coupled to the protrusion 220. The spacing adjustor 223 may include coupling bumps 224 formed on a rear surface thereof to be detachably coupled to the coupling slots 222 and fixing bump fitting holes 225 formed on a front surface thereof as shown in FIG. 7. In this case, the fixing bumps 36 may be fitted into the fixing bump fitting holes 225, and the coupling bumps 224 may be fitted into the coupling slots 222 to couple and fasten the adjustor 30 to the protrusion 220, so that the upper guard 11 and the lower guard 12 remain in a closed position, thereby preventing the user from mouth breathing.

Figure 10:
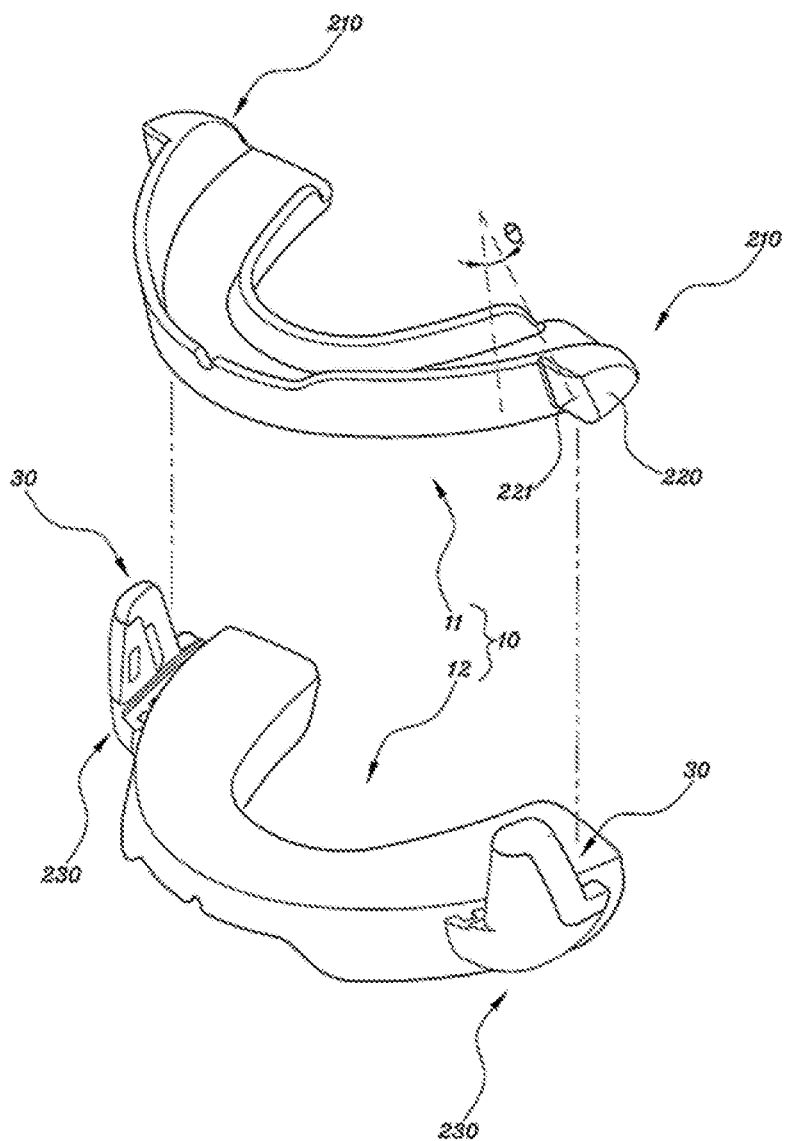
FIG. 10 is an exploded perspective view illustrating a TMJ correction apparatus, wherein an upper guard and a lower guard are separated from each other, and an adjustor as illustrated in FIG. 9 applies, according to an embodiment of the present disclosure.
Figure 11:
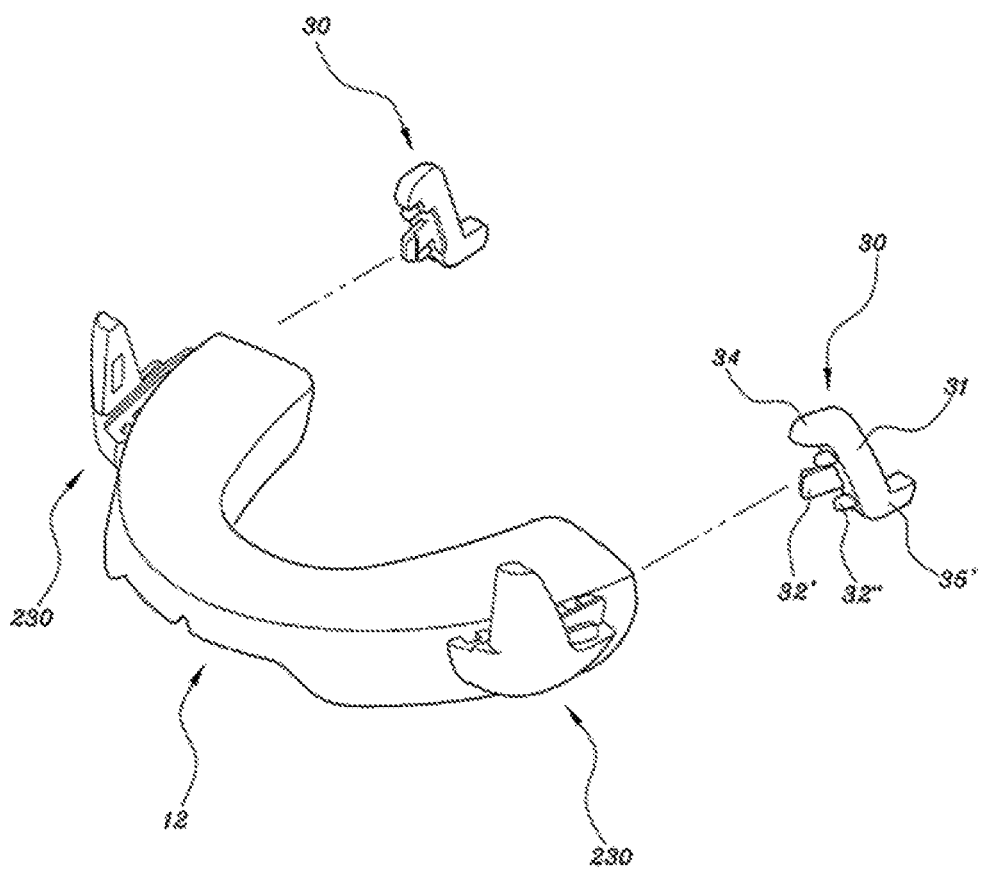
FIG. 11 is an exploded perspective view illustrating a lower guard of a TMJ correction apparatus, wherein an adjustor as illustrated in FIG. 9 applies, according to an embodiment of the present disclosure.
Figure 12:
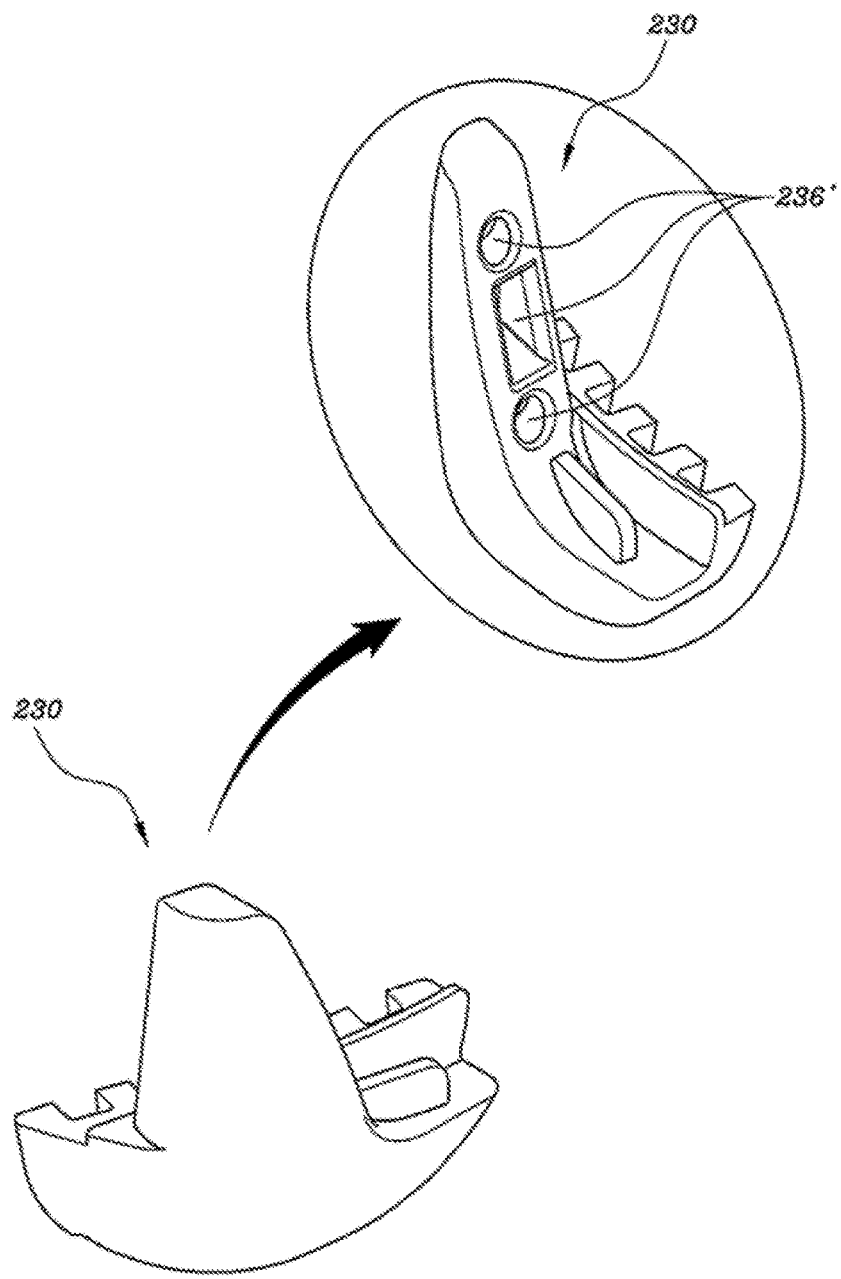
FIG. 12 is an expanded view illustrating a lower coupler of a TMJ correction apparatus when an adjustor as illustrated in FIG. 9 applies, according to an embodiment of the present disclosure.
Figure 13:
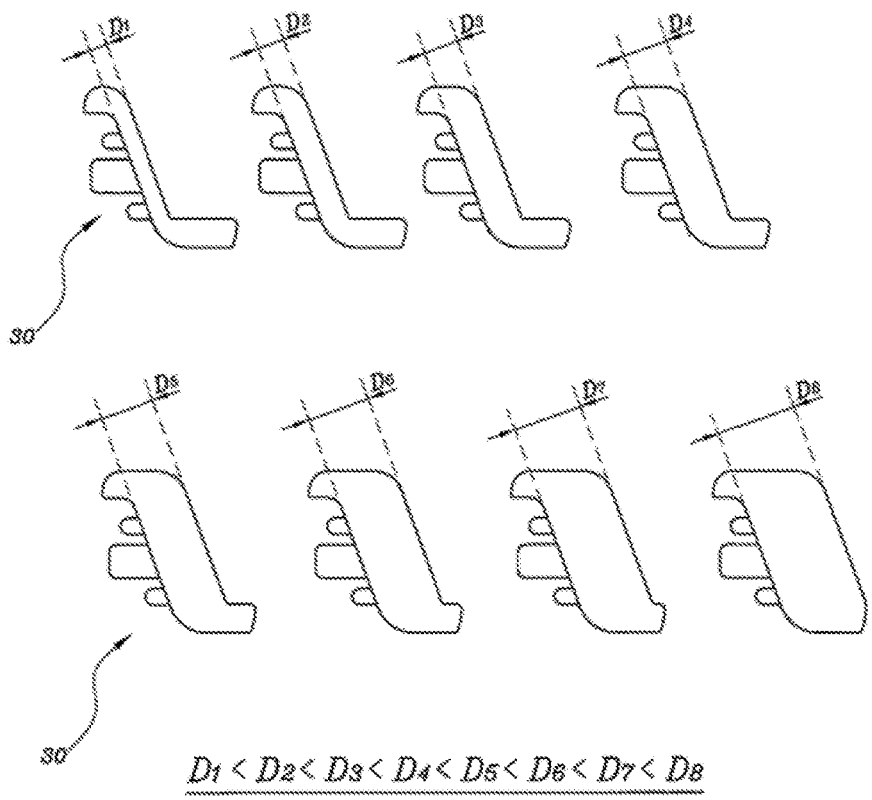
FIG. 13 is a view illustrating adjustors with different thicknesses in a TMJ correction apparatus, wherein adjustors as illustrated in FIG. 9 apply, according to an embodiment of the present disclosure.

FIG. 9 is a perspective view illustrating an adjustor of a TMJ correction apparatus according to an embodiment of the present disclosure. FIG. 10 is an exploded perspective view illustrating a TMJ correction apparatus, wherein an upper guard and a lower guard are separated from each other, and an adjustor as illustrated in FIG. 9 applies, according to an embodiment of the present disclosure. FIG. 11 is an exploded perspective view illustrating a lower guard of a TMJ correction apparatus, wherein an adjustor as illustrated in FIG. 9 applies, according to an embodiment of the present disclosure. FIG. 12 is an expanded view illustrating a lower coupler of a TMJ correction apparatus when an adjustor as illustrated in FIG. 9 applies, according to an embodiment of the present disclosure. FIG. 13 is a view illustrating adjustors with different thicknesses in a TMJ correction apparatus, wherein adjustors as illustrated in FIG. 9 apply, according to an embodiment of the present disclosure.

According to an embodiment of the present disclosure, the adjustor 30 may include a body 31, coupling mechanisms 32' and 32" protruding frontward from a center portion of the hod 31, a guide 33 extending frontward from an upper portion of the body 31 to form a bent portion 34, and a supporting portion 35' extending rearward from a lower portion of the body 31. As shown in FIG. 9, the coupling mechanisms each 32" may be shaped as a cylindrical column with a rounded tip, and the coupling mechanism 32' may have an end portion bent in a direction (e.g., Y direction) substantially perpendicular to the extension direction (e.g., X direction) of the coupling mechanism 32'. In this case, the coupling hole 235 may be excluded from the lower coupler 230. Although two coupling mechanisms 32" are provided herein for the purpose of description, embodiments of the present disclosure are not limited thereto. For example, one or three or more coupling mechanisms 32" may be provided.

According to embodiments of the present disclosure, there are provided TMJ correction apparatuses that may treat the user's snoring and teeth correction. According to an embodiment of the present disclosure, the adjustor of the TMJ correction apparatus may be replaced with another adjustor with a different thickness depending on the condition or process of correction of the user's snoring or teeth. Such exchange or replacement may occur periodically, and thus, data for proper treatment may be accumulated, providing the user with a treatment process optimized for the patient's condition.

According to embodiments of the present disclosure, there are provided TMJ correction apparatuses that may treat the user's snoring and teeth correction. According to an embodiment of the present disclosure, the adjustor of the TMJ correction apparatus may be replaced with another adjustor with a different thickness depending on the condition or process of correction of the user's snoring or teeth. Such exchange or replacement may occur periodically, and thus, data for proper treatment may be accumulated, providing the user with a treatment process optimized for the patient's condition.

While the inventive concept has been shown and described with reference to exemplary embodiments thereof, it will be apparent to those of ordinary skill in the art that various changes in form and detail may be made thereto without departing from the spirit and scope of the inventive concept as defined by the following claims.

What is claimed is:

1. A temporomandibular joint (TMJ) correction apparatus comprising:
an upper guard including an upper coupler provided at an end of the upper guard, the upper coupler including a protrusion projecting laterally;
a lower guard including a lower coupler provided at an end of the lower guard; and
an adjustor detachably coupled with the lower coupler and supported by the protrusion, wherein the adjustor includes a body, first coupling mechanism and second coupling mechanism protruding frontward from a center portion of the body, a guide extending upward and downward from the body, a bent portion extending frontward from an upper portion of the guide, and a supporting portion extending rearward from a lower portion of the guide, wherein the second coupling mechanism includes an end portion bent laterally.

2. The TMJ correction apparatus of claim 1, wherein the lower coupler includes a side fixture fixed to a side surface of the lower guard and a lower wing positioned ahead of the side surface and coupled with the adjustor.

3. The TMJ correction apparatus of claim 2, wherein the side fixture includes a plurality of protrusions and depressions, and a fixing hole is formed in the side surface of the lower guard, and wherein the plurality of protrusions and depressions are fitted into the fixing hole.

4. The TMJ correction apparatus of claim 2, wherein a rear surface of the lower wing is inclined at an acute angle with respect to a Z direction.

5. A TMJ correction apparatus, comprising:
an upper guard including an upper coupler provided at an end of the upper guard, the upper coupler including a protrusion projecting laterally;
a lower guard including a lower coupler provided at an end of the lower guard;
an adjustor detachably coupled with the lower coupler and supported by the protrusion; and
a spacing adjustor between the adjustor and the protrusion, wherein the spacing adjustor includes a coupling bump on a rear surface thereof, and the protrusion includes a coupling slot on a front surface thereof, and wherein the coupling bump of the spacing adjustor is fitted into the coupling slot of the protrusion.

6. The TMJ correction apparatus of claim 1, wherein the adjustor is exchangeable and has a predetermined thickness suited for a condition or process of correcting a jaw of a user wearing the TMJ correction apparatus.

7. The TMJ correction apparatus of claim 6, wherein the predetermined thickness of the adjustor differs depending on the condition or process of correcting the jaw.

8. The TMJ correction apparatus of claim 1, wherein a front surface of the protrusion is inclined at an acute angle with respect to a Z direction.

9. The TMJ correction apparatus of claim 1, wherein the adjustor is coupled or fastened to the protrusion to prevent the upper guard and the lower guard from opening.

10. The TMJ correction apparatus of claim 9, wherein the adjustor includes a fixing bump on a rear surface of the body, and the protrusion includes a coupling slot on a front surface thereof, and wherein the fixing bump is fitted into the coupling slot of the protrusion.

11. The TMJ correction apparatus of claim 5, wherein the adjustor includes a fixing bump on a rear surface of the body, the protrusion includes a coupling slot on a front surface thereof, and the spacing adjustor includes a fixing bump fitting hole on a front surface thereof, and wherein the fixing bump is fitted into the fixing bump fitting hole, and the coupling bump is fitted into the coupling slot of the protrusion.

\* \* \* \* \*